United States Patent [19]

Müller

[11] 3,968,257

[45] July 6, 1976

[54] PROCESSES FOR THE PRODUCTION OF PROTEIN-CONTAINING NUTRIMENTS AND FODDERS

[76] Inventor: Hans Müller, 8708 Mannedorf, Zurich, Switzerland

[22] Filed: June 9, 1975

[21] Appl. No.: 585,291

Related U.S. Application Data

[63] Continuation-in-part of Ser. No. 392,806, Aug. 29, 1973, abandoned.

[30] Foreign Application Priority Data

| Sept. 6, 1972 | Switzerland | 13177/72 |
| Oct. 13, 1972 | Switzerland | 15058/72 |
| Apr. 16, 1973 | Switzerland | 5384/73 |

[52] U.S. Cl. ................................ 426/41; 195/82
[51] Int. Cl.$^2$ .................................... A23C 21/00
[58] Field of Search .............. 195/82; 426/41, 42, 426/55, 56; 210/2, 11

[56] References Cited

UNITED STATES PATENTS

| 2,809,113 | 10/1957 | Stimpson et al. | 426/41 |
| 3,751,338 | 8/1973 | Farris | 195/82 |

OTHER PUBLICATIONS

Michaels "New Separation Technique for the CPI" Chem. Eng. Progress vol. 64 No. 12 1968 pp. 31–43.

*Primary Examiner*—A. Louis Monacell
*Assistant Examiner*—R. B. Penland
*Attorney, Agent, or Firm*—Michael J. Striker

[57] ABSTRACT

Processes for the production of essentially solid nutriments and fodders containing a high content of proteins by the cultivation of a yeast on a liquid culture medium consisting of whey containing at least a substantial portion of its original soluble proteins and thereafter separating from the resulting brew the solids consisting of yeast cells and the original soluble proteins or products of the original soluble proteins by means of an ultrafilter provided with one or more membranes that are essentially impervious to soluble proteins and subsequently drying the said solids.

The preliminary separation of the soluble proteins from the whey by centrifugal separation or by ultrafiltration, as described in the prior art, is avoided. In such prior ultrafiltration processes, the membranes of the ultrafilter become clogged with the soluble proteins, thereby retarding and ultimately stopping the filtration. The brew that is produced in accordance with the processes of the present invention which contains yeast cells together with the original soluble proteins or products thereof can be separated in an ultrafilter at a faster rate than the soluble proteins could have been preliminarily separated from the whey and the ultrafilter membranes do not become clogged with the solids that are thus separated.

5 Claims, No Drawings

PROCESSES FOR THE PRODUCTION OF PROTEIN-CONTAINING NUTRIMENTS AND FODDERS

CROSS-REFERENCE TO RELATED APPLICATION

This application is a continuation-in-part of my application Ser. No. 392,806 filed Aug. 29, 1973, now abandoned.

BACKGROUND OF THE INVENTION

Nutriments and fodders have heretofore been produced by propagating Candida yeasts on molasses. The yeast cells that are thus grown are separated from the resulting brew by centrifugation or conventional filtration and dried, and the dried product is used as animal fodder or fodder supplement. Candida yeast contains between 40 and 50% by weight of protein, dependent upon the strain and the conditions under which it was cultivated or grown.

The production of protein-containing animal fodders or fodder supplements by cultivation of yeasts and similar microorganisms on whey has also been described, for example, in U.S. Pat. No. 2,809,113. However in the process described in that patent, the brew is heated so as to release the cell substances of the yeast and the liquid that is then separated from the solids is concentrated and the concentrated solution is spray-dried.

Processes have also been described for fractionating or separating the soluble proteins that are present in whey by ultrafilters provided with membranes that are impermeable to the soluble proteins and thereafter the filtered whey from which the soluble proteins have thus been separated is used for cultivation of yeast to produce protein-containing animal fodders and fodder supplements. Such ultrafiltration processes are described in papers by Roualeyn I. Fenton-May and Charles G. Hill, Jr., and Clyde H. Amundson, entitled "Use of Ultrafiltration/Reverse Osmosis Systems for the Concentration and Fractionation of Whey" published in Journal of Food Science, volume 36, pages 14–21 (1971), and by I. K. Nielsen, A. G. Bundgaard, O. J. Olsen, and R. F. Madsen, entitled "Reverse Osmosis for Milk and Whey", published in Process Biochemistry, September 1972, pages 17–20. In such ultrafiltration processes the soluble proteins of whey become entrained in the membranes, thereby retarding or slowing and ultimately stopping the filtration.

Heretofore, in using whey as a medium for the propagation of yeasts, the cells of which are usually separated from the brew by means of centrifugal separators, the filtrate or waste water is generally contaminated with the soluble proteins or products thereof that are formed during the cultivation of the yeast. In order not to contaminate the environment, methods for the preliminary removal of the soluble proteins, such as the foregoing ultrafiltration processes, and subsequent removal of the salts by centrifugation, have been considered. Such treatment nonetheless are costly and uneconomical.

SUMMARY OF THE INVENTION

The principal object of the present invention is to provide a process in which the use of centrifugal separators that are required in prior processes is avoided and, in contrast to prior products, which normally had a protein content between 45 and 50 %, to produce nutriments and fodders having higher contents of protein.

In contrast to prior processes in which the soluble proteins were first separated by ultrafiltration, the soluble proteins in the processes of the present invention are left in the whey and the yeast is then cultivated in the whey containing these soluble proteins. Instead of clogging the membranes of the ultrafilter which normally results when the soluble proteins are preliminarily separated, the yeast cells that are produced surprisingly permit faster filtration of the solids from the brew and the membranes of the ultrafilter do not become clogged with the solids that are present in the brew.

The solids that are produced in accordance with the processes of the present invention consist of yeast cells and associated soluble proteins and products of the soluble proteins, which solids have a higher protein content than those previously produced by cultivation of the microorganism on molasses or on a whey from which the soluble proteins had been separated. Although it was expected that yeast cells would clog the membranes of ultrafilters, the yeast products of the processes of the present invention surprisingly were found actually to facilitate the filtration, perhaps in a manner similar to that of a filter aid, and actually did not clog the membrane.

DETAILED DESCRIPTION AND PREFERRED EMBODIMENT OF THE INVENTION

The example which follows is a preferred embodiment of the invention that was selected solely for purposes of illustration and consequently is not to be construed as restrictive of the invention or its scope.

EXAMPLE

A clear whey from a cheese factory containing about 4.2% by weight of lactose and about 0.7% by weight of soluble proteins or lactalbumin is inoculated in a fermentor with a culture of Saccharomyces fragilis yeast. This organism propagates in this culture and converts the carbohydrates therein into proteins. Essential nutrient salts are added to this culture and the cultivation of the yeast is carried out essentially as described in Example 1 of U.S. Pat. No. 2,809,113.

After the cultivation or fermentation has been concluded, the entire resulting suspension or slurry containing the yeast cells as well as the original soluble proteins and products to which the original soluble proteins were converted is subjected to ultrafiltration. The ultrafiltration apparatus or ultrafilter that is used for this purpose includes a series of ultrafiltration modules similar to those described in the paper by I. K Neilsen et al that was referred to hereinbefore which include porous cellulose acetate membranes that are impervious to particles of soluble proteins which have molecular weights between approximately 5,000 and 10,000 and are between 1000 and 10,000 times smaller than particles that are retained by conventional filters.

A superatmospheric pressure of approximately 5 atmospheres is applied during the ultrafiltration step and the flow of the slurry through the ultrafilter is maintained at a rate between 10 and 30 meters per second to maintain a throughput between 18 and 25 liters per square meter per hour.

No plugging or clogging of the membranes was observed when such an ultrafilter was operated in this manner for a period of 24 hours.

The amount of solids that is thus separated from the liquid or brew is equivalent to about 5% of the original volume of the brew.

Water is then added to the mass of solids and the resulting slurry is resubjected to ultrafiltration to wash therefrom salts that are still retained by the solid mass. The solid mass is then dried in a drum dryer.

The solid products that are thus obtained contain between 55 and 60% by weight of proteins which include, besides the cells of yeasts that were thus grown, the original soluble proteins or products produced from the original soluble proteins.

COMPARATIVE EXAMPLE

The same whey and ultrafilter that is described in the preceding Example is used in this comparative example. However, the original whey is first subjected to ultrafiltration in the conventional manner, as described in the paper by I. K. Neilsen et al. that was referred to hereinbefore, to separate therefrom the soluble proteins amounting to 0.7% by weight of the whey.

During the ultrafiltration step the flow of the slurry of yeast cells through the filter is maintained at a rate between 10 and 30 meters per second as in the foregoing Example but the throughput is only approximately 12 liters per square meter per hour, which is less than one-half the throughput in the foregoing Example. The membranes in the ultrafilter however clog after a period between 15 and 18 hours and must be cleaned by an enzymatic treatment and often be replaced with new membranes.

The filtrate containing the lactose together with added essential nutrient salts is then inoculated with the same culture of Saccharomyces fragilis and grown therein under the same conditions and recovered and dried as in the foregoing Example. The solid product that is thus obtained contains only 45 to 50% by weight of proteins.

The vitamins that are produced by cultivation of the yeast are often bound with the soluble protein and are consequently found in the dried yeast produced in the processes of the present invention, whereas they are usually lost in the waste water in the conventional process such as that which is described in the foregoing comparative example.

Furthermore the waste water from the processes of the present invention from which the soluble proteins and extracellular enzymes had been separated have a maximum biochemical oxygen demand of 1500 parts per million, whereas the waste water from conventional processes has a biochemical oxygen demand between 10,000 and 12,000 parts per million.

Although membranes formed of cellulose acetate were specified herein, it is to be understood that a wide range of membranes formed from other plastic materials and of different permeabilities are available and that these membranes are relatively specific as to the molecular weight of the particles that they are capable of holding back and passing.

Although Saccharomyces fragilis was used in the foregoing example, other species of saccharomyces such as Saccharomyces flava lactis, Saccharomyces Kefir, and Saccharomyces lactis, for example, may be used to produce the protein-rich nutriments or nutriment supplements of the present invention.

The whey that is used should be a clear solution and should normally be passed through a conventional filter press, centrifugal separator, or other suitable apparatus to separate therefrom any particles having a size greater than a diameter of between 5 and 10 microns, and then further filtered after a filter aid such as kieselguhr or diatomite has been added thereto.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended

1. In a process for the production of an essentially solid protein-rich nutriment and fodder from whey which comprises propagating a lactose-fermenting yeast of the genus Saccharomyces in a liquid whey, the improvement which comprises cultivating the yeast in a whey containing at least a substantial portion of its original soluble proteins and, after conclusion of the propagation, separating the solids from the resulting brew by means of an ultrafilter provided with one or more ultrafiltration membranes that are essentially impervious to soluble proteins, and subsequently drying the said solids.

2. A process as defined in claim 1 in which the yeast is *Saccharomyces fragilis*.

3. A process as defined in claim 1 in which water is added to the solids that were separated from the fermented brew and subjecting the resulting slurry to a second ultrafiltration step to wash from the separated solids any remaining salts.

4. A process as defined in claim 1 in which the solids that are separated from the cultured whey are dried by spray-drying or in a drum dryer.

5. A process as defined in claim 1 in which the whey upon which the yeast is propagated contains substantially all of the soluble proteins that were originally present therein.

* * * * *